(12) United States Patent
Wietelmann et al.

(10) Patent No.: US 7,674,911 B2
(45) Date of Patent: Mar. 9, 2010

(54) METHOD FOR THE PRODUCTION OF HYDROGEN-BIS (CHELATO) BORATES AND ALKALI METAL-BIS (CHELATO) BORATES

(75) Inventors: Ulrich Wietelmann, Friedrichsdorf (DE); Uwe Lischka, Niedereschbach (DE); Klaus Schade, Wiesbaden (DE); Jan-Christoph Panitz, Frankfurt am Main (DE)

(73) Assignee: Chemetall GmbH, Frankfurt (DE)

( * ) Notice: Subject to any disclaimer, the term of this patent is extended or adjusted under 35 U.S.C. 154(b) by 260 days.

(21) Appl. No.: 11/717,969

(22) Filed: Mar. 14, 2007

(65) Prior Publication Data
US 2007/0166622 A1 Jul. 19, 2007

Related U.S. Application Data

(62) Division of application No. 10/467,838, filed as application No. PCT/EP02/01640 on Feb. 15, 2002, now Pat. No. 7,208,131.

(30) Foreign Application Priority Data
Feb. 22, 2001 (DE) ................................. 101 08 608

(51) Int. Cl.
*C07D 231/00* (2006.01)
(52) U.S. Cl. .................................................. 548/110
(58) Field of Classification Search ................. 548/110
See application file for complete search history.

(56) References Cited

U.S. PATENT DOCUMENTS 5,886,196 A * 3/1999 Furbringer .................. 549/213

* cited by examiner

*Primary Examiner*—Rei-tsang Shiao
(74) *Attorney, Agent, or Firm*—Fulbright & Jaworski L.L.P.

(57) ABSTRACT

Methods are described for the production of hydrogen-bis (chelato)borates of the general formula $H[BL^1L^2]$ and of alkali metal-bis(chelato)borates of the general formula $M[BL^1L^2]$ where
M=Li, Na, K, Rb, Cs
$L^1$=—OC(O)—$(CR^1R^2)_n$—C(O)O—  or  —OC(O)—$(CR^3R^4)$—O—
where n=0 or 1,
$R^1$, $R^2$, $R^3$, $R^4$ independently of one another denote H, alkyl, aryl or silyl,
$L^2$=—OC(O)—$(CR^5R^6)_n$—C(O)O—  or  —OC(O)—$(CR^7R^8)$—O—
where n=0 or 1,
$R^5$, $R^6$, $R^7$, $R^8$ independently of one another denote H, alkyl, aryl or silyl,
wherein the respective raw materials are mixed in solid form without the addition of solvents and are reacted. Lithium-bis (oxalato)borate, lithium-bis(malonato)borate, caesium-bis-(oxalato)borate, caesium-bis-(malonato)borate and the mixed salts lithium(lactato,oxalato)borate and lithium(glycolato,oxalato)borate for example may be produced in this way.

4 Claims, No Drawings

METHOD FOR THE PRODUCTION OF HYDROGEN-BIS (CHELATO) BORATES AND ALKALI METAL-BIS (CHELATO) BORATES

This application is a divisional application of U.S. Ser. No. 10/467,838 filed Dec. 18, 2003 now U.S. Pat. No. 7,208,131, herein incorporated by reference in its entirety, which is a §371 of PCT/EP02/01640 filed Feb. 15, 2002, which claimed priority from German Patent Application No. 101 08 608.3 filed Feb. 22, 2001.

The invention relates to a method for the production of hydrogen-bis(chelato)borates and alkali metal-bis(chelato)borates (also known as spiroborates).

Hydrogen-bis(chelato)borates $H[BL^1L^2]$ are strong protonic acids. More specifically $L^1$=—OC(O)—$(CR^1R^2)_n$—C(O)O— or —OC(O)—$(CR^3R^4)$—O— where n=0 or 1, $R^1$, $R^2$, $R^3$, $R^4$ independently of one another denote H, alkyl, aryl or silyl, $L^2$=—OC(O)—$(CR^5R^6)_n$—C(O)O— or —OC(O)—$(CR^7R^8)$—O— where n=0 or 1, $R^5$, $R^6$, $R^7$, $R^8$ independently of one another denote H, alkyl, aryl or silyl, with $L^1$=$L^2$ in the case of the previously known hydrogen-bis(chelato)borates, i.e. $R^1$=$R^5$, $R^2$=$R^6$, $R^3$=$R^7$ and $R^4$=$R^8$.

For the hydrogen-bis(oxalato)borate $H[B(C_2O_4)_2]$, a $pK_a$ value of −0.2 has been found for example in the solvent DMSO, which is approximately equivalent to the acid strength of concentrated sulfuric acid (L. Lamandé, D. Boyer and A. Munoz, *J. Organomet. Chem.* 329 (1987) 1-29). Hydrogen-bis(chelato)borates may therefore be used as cationic catalysts in organic syntheses and in polymer chemistry.

Thus, hydrogen-bis(oxalato)borate for example serves for the selective condensation of 2,3,5-trimethylhydroquinone with isophytol to form D,L-α-tocopherol (U.S. Pat. No. 5,886,196).

DE OS 1595667 describes the use of boric acid esters prepared from tetrahydroxyboric acid and aliphatic or aromatic monocarboxylic acids or dicarboxylic acids for the production of polyesters.

Since they are electrochemically stable, lithium salts of hydrogen-bis(chelato)borates may be used as conducting salts in electrolytes for lithium batteries. Thus, solutions of lithium-bis(oxalato)borate in aprotic solvents have been proposed in DE 19829030 for use as electrolyte in lithium ion batteries.

Hydrogen-bis(chelato)borates are generally formed by azeotropic removal of water from mixtures of dicarboxylic acids and boric acid or boron oxide in a solvent suitable for azeotrope formation, such as benzene, toluene or xylene (*Gmelins Handbuch der Anorgan. Chemie, Borverbindungen*, Part 33/8, 1976, p. 118, pp. 128-129 and p. 138; 4th supplementary work, Vol. 2, 1993, pp. 217-219; supplementary work to the 3rd Edition, Vol. 44, Part 13, p. 47) (L=ligand, e.g. $L^1$):

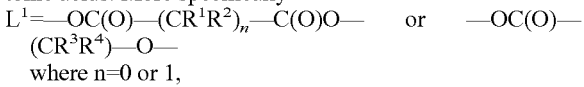

(1)

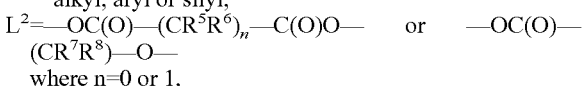

(2)

Thus for example hydrogen-bis(oxalato)borate is obtained in 70% yield by refluxing a suspension of oxalic acid and boron oxide in toluene for six hours and removing the water formed by means of a water separator (U.S. Pat. No. 5,886,196). In this specification, it is stated that trimethyl boroxine or trimethyl borate may also be used instead of boron oxide. In this case, not water but methanol is removed as byproduct.

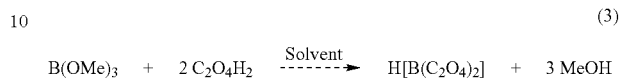

(3)

Oxalic acid reacts in a homogeneous phase with boric acid in non-aqueous solvents with a high dielectric constant, such as for example dimethylformamide, with the formation of the spiroborate-1:2 adduct. The anhydrous solid salts can be obtained therefrom by evaporation (L. Lamandé, see above).

In aqueous solution, the components boric acid and ligand $LH_2$ are present in an equilibrium that depends on the respective complex formation constants:

(4)

In general the bis-(chelato) complexes $H[BL_2]$ cannot be isolated directly in pure form from aqueous solutions, since the equilibrium (4) tends to be displaced towards the left-hand side. Consequently 1:1-complexes as a rule crystallise out when aqueous solutions containing two parts of $LH_2$ and one part of boron component such as for example $H_3BO_3$ are cooled or concentrated (E. Bessler and J. Weidlein, *Z. Naturforsch.*, 37b, 1020-1025, 1982).

A common feature of all the aforedescribed preparation methods is that they require an organic solvent. In an industrial synthesis, measures must therefore be adopted to ensure safe handling of solvents (combustibility, toxicity of aromatic compounds such as for example benzene). Also the space/time yield is comparatively low on account of the dilution accompanying the use of solvents.

Alkali metal salts $M[BL_2]$ (M=Li, Na, K, Rb, Cs) of the hydrogen-bis(chelato)borates may be obtained either by neutralising previously isolated acid $H[BL_2]$ with basic alkali metal compounds such as $M_2CO_3$, MOH, MH etc., or—which is more advantageous—directly starting from the ligands $H_2L$, a boron component, and a basic alkali metal compound.

The most common method consists—by analogy to the reactions (1) and (2) given above—in suspending the components in a solvent and separating the water azeotropically (Bessler, Weidlein, see above):

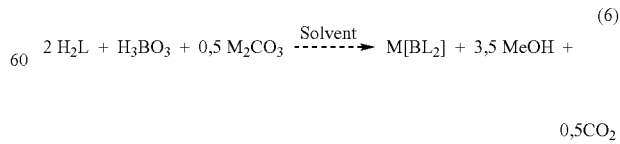

(5)

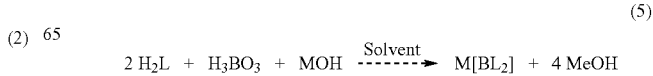

(6)

Those solvents that form an azeotrope with water are suitable, for example benzene, toluene, xylene.

In a variant, the alkali metal may also be incorporated via the salt of the ligand (MHL or $M_2L$) or via a metal borate (e.g. $MBO_2$):

(7)
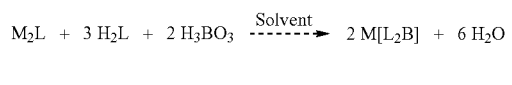

(8)
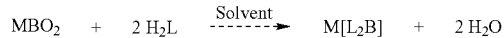

A further possible preparation consists in reacting the metal tetraalkoxy borate $M[B(OR)_4]$ with two equivalents of the ligand (DE 19829030), e.g.

(9)
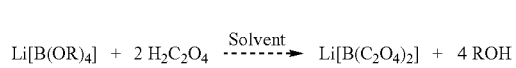

The alcohol itself (methanol, ethanol) or an aprotic, polar solvent such as for example acetonitrile may be used as the solvent.

The synthesis starting from metal tetrahydridoborates $MBH_4$ and 2 equivalents of the ligand in a solvent is known in which the metal tetrahydridoborate has a certain solubility (e.g. THF or 1,2-dimethoxyethane) (DE 19829030), e.g.:

(10)

A common feature of all the methods listed above for preparing $M[BL_2]$ compounds is that they require organic solvents and proceed at a corresponding dilution. The space/time yield is consequently relatively low.

It is finally known to prepare lithium-bis(oxalato)borate in a homogeneous aqueous solution by reactions according to (5), (6), (7) or (8) and to isolate the borate in a solid, anhydrous form after complete evaporation and vacuum drying. The disadvantage of this method is that the space/time yield is relatively low. Thus, in DE 19829030 only 185 g of product are obtained from ca. 3.1 kg of reaction solution (Example 1). The amount of water required for a homogeneous dissolution of the reaction components must be evaporated with a high energy input.

The object of the present invention is accordingly to provide a method that avoids the disadvantages of the prior art and produces the desired spiroborate compounds in good chemical yields, in particular without the use of organic solvents, and with the highest possible space/time yields.

This object is achieved by the methods disclosed in the independent claims 1, 5, 9 and 12. In this connection, the desired ligands $L^1$

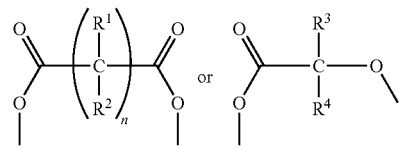

where n=0 or 1, $R^1$, $R^2$, $R^3$, $R^4$ independently of one another denote H, alkyl, aryl or silyl, with the alkyl groups preferably containing 1 to 10 C-atoms, the aryl groups being preferably monoaryl groups which may also be substituted, and the silyl groups being preferably trialkylsilyl groups, in which the alkyl groups respectively contain 1 to 4 C atoms, and optionally $L^2$ being protonated form ($H_2L^1$ and $H_2L^2$), are mixed with an oxidic boron compound and, optionally, an alkali metal raw material in solid form, without the addition of solvents and are brought to reaction by for example stirring and/or heating, with the molar ratio of the sum of the ligands $L^1$ and $L^2$ used to the amount of boron used, being preferably 2:1. Relatively small deviations from the theoretical stoichiometry (e.g. 10% above or below) are possible without greatly affecting the relevant product.

It was surprisingly found that the process products (spiroborate compounds) are formed in good yield and good purity under these predominantly heterogeneous reaction conditions. It has therefore proved unnecessary to add a solvent and homogeneously dissolve and then mix the respective reaction components, and isolate the end product. The water formed during the reaction and the water (water of crystallisation) possibly introduced with the raw materials (starting materials) is completely sufficient for the reaction to proceed. The reaction between the as a rule solid substances already partly takes place at room temperature and is completed by the removal of the water that is present or formed.

In a preferred modification of the invention, small amounts of water may, in addition; be added in order, for example, to improve the thermal conductivity or prevent dust formation. The amount of water that is added is such that the total water content of the synthesis mixture (i.e. the sum total of the water introduced with the raw materials (e.g. water of crystallisation, adhering moisture), the water of reaction and the added water) does not exceed 50 wt. % and particularly preferably is between 5 and 45 wt. %.

The removal of the water is preferably effected by distillation at elevated temperatures, particularly preferably under reduced pressure. The pressure and temperature conditions depend on the specific properties of the raw materials that are used and the end products. Preferred drying temperatures are between 80° and 180° C.

As ligands $L^1$ and/or $L^2$ there are preferably used the oxalate radical, the malonic acid radical, glycolic acid and/or lactic acid are preferably used as ligands $L^1$ and/or $L^2$.

Preferably a boron oxide, particularly preferably $B_2O_3$ or a boric acid, particularly preferably $H_3BO_3$ or $HBO_2$ is used as the oxidic boron compound.

An alkali metal carbonate, alkali metal hydrogen carbonate, alkali metal hydroxide or alkali metal oxide is preferably used for the oxidic alkali metal raw material specified in the independent claim 5. Lithium carbonate and lithium hydroxide are particularly preferred.

The method according to the invention may be carried out for example as follows:

The calculated stoichiometric amounts of the raw materials are first of all mechanically mixed at room temperature. The mixing may also take place at relatively high temperatures, e.g. 50° to 100° C., or at lower temperatures, e.g. 0° C.; however, this does not have a positive effect on the course of the reaction.

The mixing may—depending on the apparatus that is available and the scale of the reaction—take place for example by weighing out the reactants in a glass flask and mixing them with a stirring rod or by agitating the flask (e.g. rotary evaporator). In some cases it is also recommended to grind the solid components individually or in the mixture, for example in a laboratory mortar or in a disc grinding mill or rod-type vibratory grinding mill.

Particularly preferably the mixing is carried out in a mixer equipped with a slow speed stirrer or in a bladed mixer.

The acid components, i.e. the boron compound and the ligand, are preferably first of all placed in the reaction vessel and mixed. The basic metal compound that may possibly be required is then added rapidly in one go although, and this applies in particular to larger scale operations, while it is preferably being added in portions. The reaction with the metal component is exothermic; carbon dioxide is also formed when using $M_2CO_3$, for which a safe gas release device must be provided.

When using only two reaction components analogous to (1), (2) or (8), the order of the addition is not important.

After mixing the components, the total amount of water is removed by distillation. This is achieved by raising the temperature and preferably at reduced pressure.

Particularly preferred is an embodiment in which the reaction is initially carried out at normal pressure or only moderately reduced pressure (>200 mbar, preferably >500 mbar). The reaction mixture is in this case heated by means of external heating, to an internal temperature of about 90° to 110° C. (in the case of lithium-bis(oxalato)-borate to 120° C.), the greater part of the water rapidly distilling off. Only when most of the water (>ca. 75%) has been removed is the pressure gradually reduced (down to e.g. <30 mbar or lower). The final drying conditions depend on the thermal stability of the spiroborate that is obtained. In general the reactants are finally mixed under a maximum vacuum and at a product temperature of 100° to 180° C. (in the case of lithium-bis (oxalato)borate up to 200° C.) until at a constant weight. This phase may—depending on the type of drying apparatus—last ca. 0.5 to 5 hours.

When using a drying apparatus having an insufficient mixing intensity (e.g. a rotary evaporator) it may happen that the reaction matter strongly agglomerates or completely solidifies. In this case it cannot be guaranteed that the synthesis reaction will proceed to completion. The evaporative concentration then has to be interrupted and the reaction material comminuted (e.g. with a mortar). This procedure is preferably carried out at the end of the first reaction phase, i.e. before reducing the pressure to <200 to 500 mbar.

The process products are generally formed in yields of >95%: they have a low water content (<0.5%) and a purity of >95%.

The method according to the invention is in particular suitable for the production of lithium-bis(oxalato)borate. This method variant is described hereinafter by way of example: oxalic acid dihydrate (or anhydrous oxalic acid) is mixed with boric acid (which is preferably ground) in a molar ratio of (1.98 to 2.04): 1. 1.01 to 1.05 moles of lithium in the form of an oxidic lithium compound (lithium hydroxide, lithium hydroxide monohydrate or lithium carbonate) and a maximum of 2 moles of water per mole of boric acid are then added. The mixture is heated to a maximum temperature of 120° C. while stirring at a pressure of initially 500 to 1000 mbar, most of the water (preferably at least 75% of the total amount of water present in the reaction mixture) distilling off to leave a finely crystalline, stirrable product. A further 0.005 to 0.04 mole of the oxidic lithium compound per mole of boric acid used may be added at the end of this first drying phase.

The drying (duration of preferably 2 to 5 hours) is continued under a higher vacuum (1 to 500 mbar, preferably 1 to 50 mbar) and at temperatures of 150° to 200° C., preferably 160° to 180° C., the reaction mixture being dried further for at least one hour after the final temperature has been reached. When choosing the drying temperature, it should be borne in mind that lithium-bis(oxalato)borate is thermally relatively stable and can withstand somewhat higher drying temperatures than the other alkali metal-bis(chelato)borates.

The reaction and the drying are preferably carried out in a paddle-wheel dryer or kneader-type dryer that is resistant to corrosion by oxalic acid.

The advantage of the method according to the invention is that no organic solvent is used, and water is not added or is only added in minor amounts. The complicated step involving an azeotropic distillation can thus be omitted and only relatively minor amounts of water have to be removed from the reaction mixture. Additionally, the method according to the invention proves to be so versatile that for the first time even borates with different ligands ($L^1 \neq L^2$, where the molar ratio $L_1:L_2:B$ of the substances employed is 1:1:1) or borate mixtures ($L^1 \neq L^2$, where the molar ratio $L_1:L_2$ is not equal to 1, but the sum total of moles of $L_1$ and $L_2$ per mole of B that is used is however 2) can be produced.

The hydrogen-bis(chelato)borates produced by the method according to the invention are used as protonic acid catalysts in organic chemistry, and the alkali metal-bis(chelato)borates are used as electrolytes for electrochemical storage systems.

The invention is described in more detail hereinafter with the aid of examples.

EXAMPLE 1

Production of Lithium-Bis(Oxalato)Borate in a Mixer 549 g of oxalic acid dihydrate (superpure, Merck, 4.36 moles) and 134 g (2.18 moles) of ground boric acid were placed at room temperature in a halar-coated 2 l capacity double jacket steel reactor equipped with an anchor stirrer, distillation bridge, internal thermometer and proportioning device for solids. 84 g (1.14 moles) of superpure lithium carbonate were added within ca. 10 minutes through a measuring bulb while stirring slowly. A gas was formed and the temperature of the reaction mixture rose to about 27° C.

The jacket temperature was then slowly increased (within 1 hour) to 110° C. while gently stirring and a slight vacuum was applied (pressure in the reaction vessel ca. 800 mbar). After the internal temperature reached about 90° C., the water began to distil off. After the distillation process had significantly abated (ca. 1.5 hours) the reactor temperature was first of all raised to 130° C. and finally to 160° C. and the pressure was further reduced. The reaction mixture was finally stirred for 2 hours at an internal temperature of 145° C. and a pressure of 15 mbar.

After cooling to room temperature the reactor was emptied.

Yield: 405 g of white powder (corresponds to 96% of theoretical)

Analysis (mmoles/g): B 5.15; Li 5.3; water (according to the modified Karl Fischer method) 0.4%; $\delta^{11}B$ (solution in THF): only signal at 7.6 ppm

EXAMPLE 2

Production of Lithium-Bis(Malonato)Borate in a Rotary Evaporator 16.75 g (271 mmoles) of boric acid and 56.36 g (542 mmoles) of malonic acid were ground together in a mortar and then transferred to a 500 ml glass flask. 10.00 g of superpure lithium carbonate (135 mmoles) were added and then heated to 120° C. under reduced pressure (ca. 900 mbar) and kept at this temperature for 1.5 hours.

At the end of this time, the vacuum was released and the contents of the flask were comminuted with a mortar. The powdery product was returned to the flask and dried for a further 2.5 hours at 120° C. under a vacuum (finally at 15 mbar).

Yield: 57.1 g (corresponds to 97% of theoretical) of finely powdered, white product Analysis (mmoles/g): Li 4.50; B 4.80; $\delta^{11}B$ (solution in DMF): 3.7 ppm

EXAMPLE 3

Production of Hydrogen-Bis(Oxalato)Borate in a Rotary Evaporator 40.0 g (647 mmoles) of ground boric acid and 163.1 g (1294 mmoles) of oxalic acid dihydrate were added to a 500 ml glass flask and heated initially at normal pressure. When the temperature reached about 100° C. the mixture began to melt. A clear melt formed at an internal temperature of 120° C., from which water slowly distilled off. The distillation rate was increased by reducing the pressure (initial pressure in the reaction vessel ca. 700 to 500 mbar). After ca. 1 hour practically no more distillate came over and the contents of the flask solidified to a white solid.

The distillation procedure was interrupted, the water formed was weighed (55.2 g) and the contents of the flask were mechanically comminuted (using a mortar). The ground reaction material was then returned to the flask and reheated (135° C. at ca. 20 mbar). Under these conditions a relatively small amount of a colourless sublimate was deposited on the cooler parts of the distillation apparatus. After drying for about 2 hours under the aforementioned conditions, the reaction material was cooled under a dry protective gas atmosphere.

Yield: 108 g of colourless, crystalline product (89%)

Analysis: B=5.25 mmoles/g $\delta^{11}B$ (solution in 1,2-dimethoxyethane): 7.6 ppm $\delta^{1}H$ (solution in 1,2-dimethoxyethane): 11.99 ppm $\delta^{13}C$ (solution in 1,2-DME): 158.85 ppm

EXAMPLE 4

Production of Sodium-Bis(Oxalato)Borate in a Rotary Evaporator 46.37 g of boric acid (750 mmoles), 189.11 g of oxalic acid dihydrate (1500 mmoles) and 41.73 g of sodium carbonate (394 mmoles) were weighed out into a 1 l capacity round-bottomed flask and stirred at a bath temperature of 140° C. and an initial pressure in the round-bottomed flask of 900 mbar. After 1 hour, water no longer condensed and the contents of the flask had agglomerated to form a solid mass. The reaction matter was removed from the flask, ground in a mortar, and returned to the flask. The product was dried for a further 4 hours at a bath temperature of 140° C. and under a pressure reduced in stages (finally 20 mbar).

Yield: 152 g (97%)

Analysis: $\delta^{11}B$ (solution in N-methylpyrrolidone): 7.6 ppm

EXAMPLE 5

Production of Lithium(Malonato,Oxalato)Borate in a Rotary Evaporator 90.05 g of oxalic acid, 104.3 g of malonic acid and 61.8 g of boric acid (in each case 1 mole) were ground in a mortar and added to a 1 l capacity glass flask. After adding 38.1 g (0.516 mole) of lithium carbonate the mixture was heated on a rotary evaporator at an oil bath temperature of initially 100° C., rising subsequently to 120° C., and under a pressure in the glass flask of 900 mbar. When the temperature reached 110° C. the mixture began to boil vigorously. After stirring for 2 hours at ca. 120° C. and at a final pressure of 300 mbar the reaction mixture solidified to form a solid mass that was ground in a mortar after cooling.

The powdered product was then dried once more to constant weight (3 hours) at an oil bath temperature of 120° C. under a full vacuum (9 bar).

Yield: 206 g (99.5%) of a pale cream-coloured powder

Analysis: $\delta^{11}B$ (THF solution): 7.6 ppm (11%); 5.5 ppm (71%); 3.7 ppm (17%)

The end product was a mixture containing the mixed spiroborate with $\delta^{11}B=5.5$ ppm as main component. This was obtained in pure form by recrystallisation.

EXAMPLE 6

Production of Lithium(Lactato,Oxalato)Borate in a Rotary Evaporator 49.6 g of boric acid (802 mmoles) and 80.1 g of 90% aqueous lactic acid solution (800 mmoles), 100.9 g of oxalic acid dihydrate (800 mmoles) as well as 33.8 g (806 mmoles) of lithium hydroxide monohydrate were placed in a 1 l capacity glass flask and kept first of all for 45 minutes at 700 mbar and 110° C. When the temperature exceeded ca. 100° C., a melt/solution formed with a small amount of solids remaining, and water began to distil off. After the specified time the oil bath temperature was raised to 126° C. and the pressure was reduced to 300 mbar. After stirring for 60 minutes under these conditions, the melt solidified into a lumpy solid.

The drying procedure was interrupted, the reaction mixture was ground in a mortar, and the comminuted product was then dried for 3 hours at 110° C. and at a final pressure of 10 mbar.

Yield: 154.1 g (99%) of cream-coloured powder $\delta^{11}B$ (DMF solution): 8.9 ppm (main product)

10.2 ppm (ca. 3%, lithium-bis(lactato)borate)

7.5 ppm (ca. 2%, lithium-bis(oxalato)borate)

Thermogravimetry (TGA): start of decomposition at about 300° C.

The invention claimed is:

1. A process for the production of hydrogen-bis(chelato) borates of the formula $H[BL^1L^2]$ comprising:

mixing starting compounds $H_2L^1$ and $H_2L^2$ with an oxidic boron compound without adding a solvent to form a heterogeneous mixture, reacting the heterogeneous mixture and optionally introducing water with the raw materials, and removing water formed during the reaction, wherein $L^1$ is selected from the group consisting of —OC(O)—$(CR^1R^2)_n$—C(O)O— or —OC(O)—$(CR^3R^4)$—O—;

$R^1$, $R^2$, $R^3$ and $R^4$ are independently selected from the group consisting of H, alkyl, aryl or silyl;

$L^2$ is selected from the group consisting of —OC(O)—$(CR^5R^6)_n$—C(O)O— and —OC(O)—$(CR^7R^8)$—O—, $R^5$, $R^6$, $R^7$ and $R^8$ independently selected from the group consisting of H, alkyl, aryl and silyl;

$H_2L^1$ is selected from the group consisting of H—OC(O)—$(CR^1R^2)_n$—C(O)O—H and H—OC(O)—$(CR^3R^4)$—O—H; and $H_2L^2$ is selected from the group consisting of H—OC(O)—$(CR^5R^6)_n$—C(O)O—H or H—OC(O) $(CR^7R^8)$—O—H;

wherein $H_2L^1$ and $H_2L^2$ are optionally the same;

and n is 0 or 1.

2. The process according to claim 1, wherein water is added to the heterogeneous mixture of the starting substances, the amount of water that is added being such that the total water content of the synthesis mixture (i.e. the sum total of the amount of water introduced with the raw materials, the amount of water of reaction and the amount of added water) does not exceed 50 wt. %.

3. The process according to claim 1, wherein water is removed by distillation at temperatures up to 180° C.

4. The process according to claim 1, wherein said oxidic boron compound is selected from the group consisting of boron oxide and boric acid.

* * * * *